United States Patent [19]

Markart

[11] Patent Number: 6,063,337
[45] Date of Patent: May 16, 2000

[54] TEST STRIP FOR MEASURING DEVICE FOR OPTICALLY DETECTING THE CONCENTRATION OF A SUBSTANCE IN A BODY FLUID

[75] Inventor: Ernst Markart, Munich, Germany

[73] Assignee: LRE Technology Partner GmbH, Munich, Germany

[21] Appl. No.: 09/137,196

[22] Filed: Aug. 20, 1998

[30] Foreign Application Priority Data

Aug. 21, 1997 [DE] Germany ................ 297 15 019 U

[51] Int. Cl.⁷ ...................................................... G01N 33/49
[52] U.S. Cl. ................................. 422/58; 422/61; 422/56
[58] Field of Search ................... 422/56, 58, 61

[56] References Cited

U.S. PATENT DOCUMENTS 5,833,923  11/1998  McClintock et al. ................ 422/52
5,853,670  12/1998  Bunc ...................................... 422/100

*Primary Examiner*—Lyle A. Alexander
*Attorney, Agent, or Firm*—McCormick, Paulding & Huber LLP

[57] ABSTRACT

In a test strip for use with a measuring device for determining the concentration of a substance in a body fluid by means of an optical measuring system using a beam of light directed onto a measuring field of the measuring strip, the measuring strip is formed of a bottom layer, a cover layer and a spacer layer located between the bottom layer and the cover layer. The bottom layer has a pass through opening for the light beam and the cover layer has a drop application opening with these two openings being displaced from one another so as to be out of overlapping relationship with one another. The spacer layer has an elongated opening or recess, a portion of which overlies the pass through opening of the bottom layer and another portion of which underlies the drop application opening of the upper layer. The recess in the spacer layer also receives a web of absorbent material, which absorbent material overlies the beam pass through opening and forms the measuring field. Body fluid applied to the drop application opening is absorbed by the absorbent material of the measuring field. The material of the spacing layer may also be absorbent but has an absorption response retarded from that of the measuring field material, so that the measuring field material fills itself with the applied body fluid before a significant amount of the body fluid is absorbed by the material of the spacing layer.

1 Claim, 2 Drawing Sheets

TEST STRIP FOR MEASURING DEVICE FOR OPTICALLY DETECTING THE CONCENTRATION OF A SUBSTANCE IN A BODY FLUID

FIELD OF THE INVENTION

The invention concerns a test strip for a measuring device for optically determining the concentration of a substance in a body fluid, especially for blood sugar determination, with a carrier on which is formed a measuring field made of an absorbent material.

BACKGROUND OF THE INVENTION

Measuring devices of the previously mentioned kind have been proposed in which the test strips are first inserted into the device and then the fluid to be investigated is dropped onto the measuring field of a test strip lying inside the device. This has the advantage that the test strip is not moved between an empty or calibrating measurement and a measurement with applied fluid, so that for both of the measurements, the same measurement conditions exist. Further, only little time elapses between the application of the fluid and the carrying out of the measurement. There also does not exist the danger that the test strips, upon insertion into the device, deteriorate and thereby possibly produce false measuring results.

Further, measuring devices have been proposed in which several test strips joined to a test strip card lie in the device and always only that test strip is pulled from the device which is needed for the actual measurement. The remaining test strips, that is, the remainder of the test card, lies in a pouch in the device, with a device cover holding the pouch tightly sealed. Insofar as the measuring station in these devices is not covered, there exists the danger that stray light can falsify the measurements. Further, if one wants to provide many test strips on a test strip card, the test strip measurements must be small. This leads to the fact that the measuring fields of bordering test strips lie close to one another. Therefore, there exists the danger that the fluid dropped onto the measuring field of one test strip, through capillary action, can be absorbed into the measuring field of a neighboring test strip.

SUMMARY OF THE INVENTION

The invention has, as its object, the provision of a test strip of the initially mentioned type, which avoids the previously mentioned difficulties and whereby, even in the case of open measurement, the effect of stray light on the measurement is negligibly small, and the danger of soiling a neighboring test strip is inhibited.

This object is solved in accordance with the invention in that the carrier includes a bottom layer and a cover layer, which bottom layer and cover layer are separated from one another by a spacing layer, in that in the bottom layer a pass through opening for the measuring beam of the measuring optic system is formed, which pass through opening is covered by the measuring field, in that in the cover layer a drop application opening is formed which is so displaced relative to the measuring field that the measuring field and the drop application opening do not overlap, and in that the spacing layer has a recess, including the measuring field and the drop application opening.

If a drop of the fluid to be investigated is applied to the drop application opening, the fluid first moves into the portion of the recess in the spacing layer lying under the drop application opening. From there, the fluid, by capillary action, is absorbed into the absorbent material forming the measuring field, which lies in or above the pass through opening for the measuring beam. Since the remaining portion of the recess and, as the case may be, also the drop application opening are filled with the fluid, for example, blood, and since the measuring field itself is covered by the cover layer, there exists no danger that stray light can influence the measurement.

To inhibit that eventual excess fluid does not soil the device or a neighboring test strip, the spacing layer is preferably made of an absorbent material with an absorbency response retarded from that of the measuring field. After the material forming the measuring field has entirely filled itself with absorbed fluid, the possibly remaining fluid can be absorbed by the spacing layer.

In order to determine whether sufficient blood has been received by the measuring field, it is advantageous if the cover layer, at least in the area of the measuring field is transparent.

Further features and advantages will be apparent from the claims and from the following description, which in combination with the accompanying drawings, explains the invention by way of an exemplary embodiment.

DETAILED DESCRIPTION OF THE DRAWINGS

Figure 1:
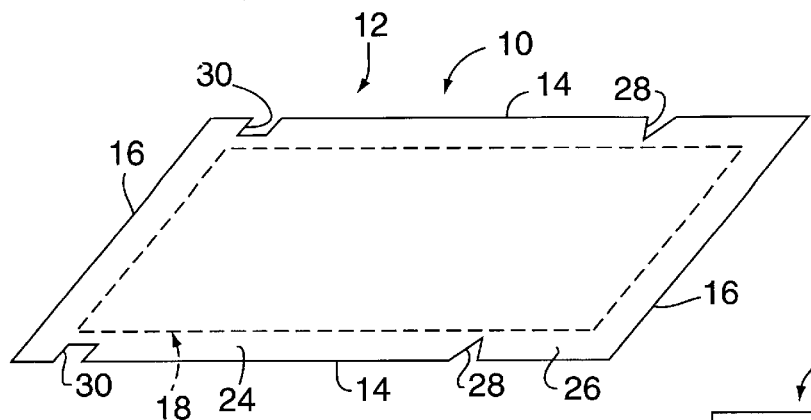

The drawings are:

FIG. 1—a schematic prospective view of a test strip package.

Figure 2:
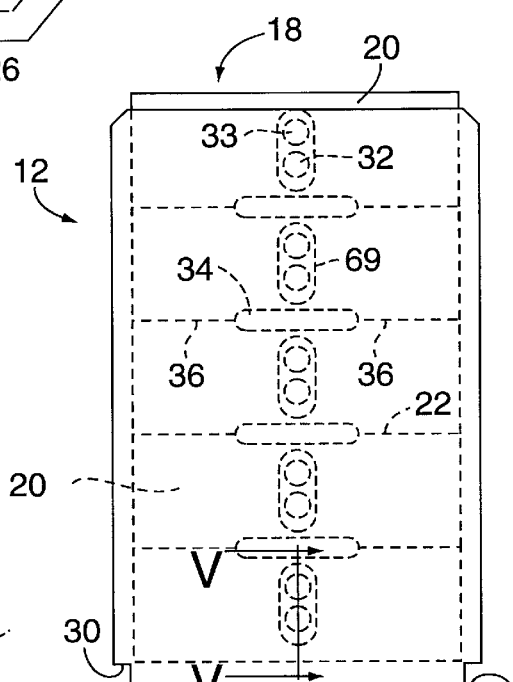

FIG. 2—a view corresponding to FIG. 1 of the test strip package after the tearing off of the head section of the package sleeve.

Figure 3:
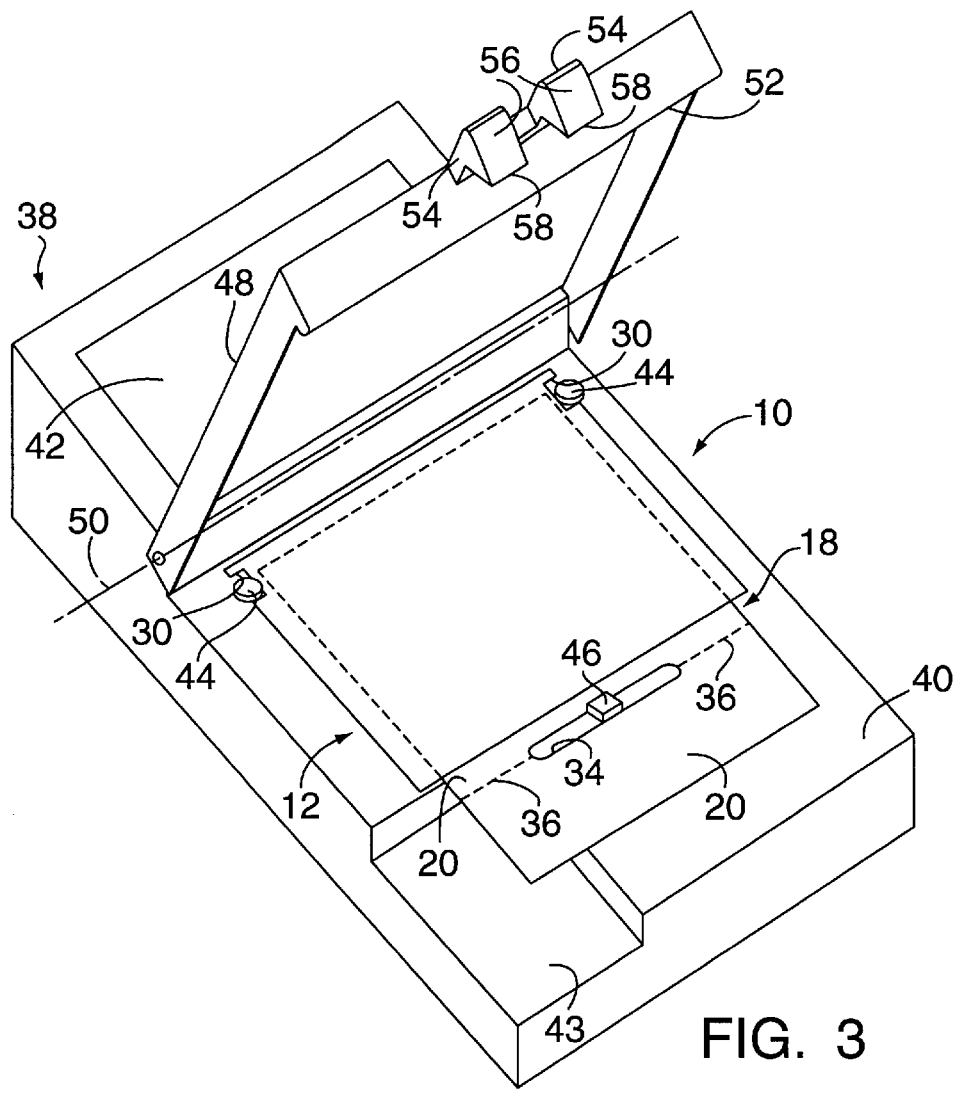

FIG. 3—a schematic prospective view of a measuring device for an optical evaluation and for use with a test strip package as illustrated in FIGS. 1 and 2, with the device having an opened cover.

Figure 4:
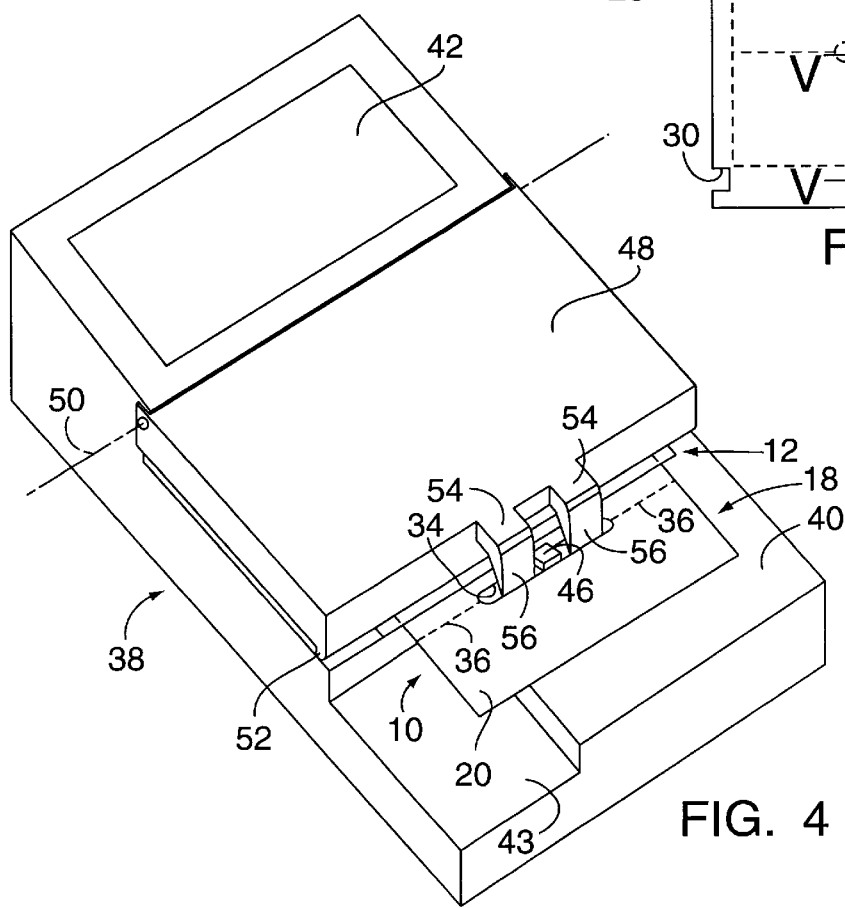

FIG. 4—a view corresponding to FIG. 3 of the measuring device with the cover closed.

Figure 5:
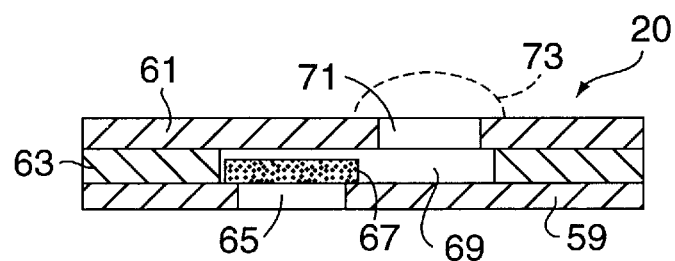

FIG. 5—a sectional view through a test strip along line V—V of FIG. 2.

DETAILED DESCRIPTION OF THE PREFERRED EMBODIMENT

FIG. 1 illustrates a test strip package indicated generally at 10. It includes a rectangular flat sleeve or bag 12 which is closed along its longitudinal edges 14 and along its transverse edges 16. It consists of two material webs or a single folded material web, wherein the open longitudinal and transverse edges 14 and 16 are glued or heat sealed to one another and the material webs are air and moisture impermeable.

The sleeve 12 serves for the reception of a rectangular test strip card 18, indicated by broken lines, having a plurality of test strips 20 which are connected to one another along tear lines 22. The test strip card 18 is described in greater detail hereinafter.

The sleeve 12 includes a main section 24 and a head section 26 separable from the main section. The separation line, along which the head section 26 is separable from the head section 24, is marked by two notches 28 lying opposite to one another along the longitudinal edges of the sleeve.

Near the end of the sleeve 12, opposite to the head section 26, two rectangular recesses 30 are formed in the longitudinal edges 14, the function of which recesses are explained in more detail below in connection with the description of the measuring device.

According to FIG. 2, each test strip 20 has a test or measuring field 32 and a drop application field 33, onto which drop application field a drop of body fluid, for example a drop of blood, can be dropped. The construction of the test strip is explained in more detail hereinafter. If the head section 26 is torn from the main section 24 of the sleeve 12, the first test strip 20 of the test card 18 projects far enough out of the main section 24 of the sleeve that it can be grasped (FIG. 2). The drop application field 32, however, lies still protected in the main section 24 of the sleeve 12. Each tear line 22 between two test strips 20 consists of a middle longitudinal slot 34 and perforation lines 36, each of which lines extends from an end of the slot to the adjacent longitudinal edge 14.

In connection with FIGS. 3 and 4, a measuring device for using the above-described test strip package 10 will now be explained. The measuring device includes a housing, indicated generally at 38, with a support or surface 40 for the test strip package 10. The housing contains, in a way known in itself, a measuring optic system and an evaluation and control circuit, both of which are not illustrated, as well as an indicator unit 42. The measuring beam of the measuring optic system passes through an opening formed in the support surface 40 below the test field 32, which test field, as illustrated in FIGS. 3 and 4, is that of a test strip 20 which has been pulled entirely out of the sleeve 12. In the test strip support surface 40 a gripping depression 43 is formed so that the test strip 10 can be more easily grasped.

As can be seen in FIG. 3, the test strip package 10 is so supported on the support surface 40 that arresting pins 44, which are provided on the support surface 40 in the vicinity of the indicator unit 42, are received in the rectangular notches 30 of the sleeve 12. In this way, the test strip 10 is fixed relative to the support surface 40. The sleeve 12 remains in place when the test strip 18 is pulled out of the sleeve 12 until a nose 46 arranged on the test strip support surface 40 enters into the slot 34 behind the first pulled out test strip 20, as is illustrated in FIG. 3. In this position, which is also shown in FIG. 4, the test field 32 lies exactly over the pass through opening for the measuring beam.

A lid or cover 48 is pivotally supported on the housing 38 for moment about a pivot axis 50 parallel to the support surface 40. The cover 48 can therefore be pivoted between a first position, illustrated in FIG. 3, in which the support surface 40 is freely accessible for the purpose of placing or removing the test strip package 10 or the sleeve 12 onto or from the support surface 40, and a second position (FIG. 4) in which the support surface 40 is partially covered. The cover 48 can be biased toward this second position by suitable non-illustrated means, so that it lies tightly onto the support surface 40.

At its edge remote from the pivot axis 50, the cover 48 has a sealing lip 52, which in the second position of the cover engages the sleeve 12 of the test strip package 10 near the open edge of the main section 24. The sealing lip 52 on one hand holds the sleeve 12 closed and, on the other hand, holds the test strip package 10 fixed to the support surface 40.

The cover 48 further on its free end remote from the pivot axis 50 carries two L-shaped elements 54 whose shorter free legs are formed as wedge shaped separating elements 56, each having a free separating edge 58. The arrangement of the elements 54 is so accomplished that upon the clapping shut of the cover 48 the separating elements 56 move precisely into the slot 34 of the tear line 32 behind the test strip 20 which has been pulled entirely from the sleeve 12. Thereby, on one hand, the test strip card 18 is further fixed to the support surface 40. On the other hand, the portion of the test strip card 18 remaining in the sleeve 12 is held fixed when the entirely pulled out test strip 20 is torn off after the carrying out of the measurement. The arrangement can also be designed that the wedge shaped separating elements can be pressed into a non-illustrated recess in the test strip support surface to thereby separate the test strips from one another.

FIG. 5 shows, in a schematic cross section, the construction of a test strip 20. Each test strip consists of three layers—namely, a bottom layer 59, a cover layer 61 and a spacing or intermediate layer 63 separating the bottom layer from the cover layer. In the bottom layer 59, a pass through opening 65 is formed for the measuring beam of the measuring optic system. The pass through opening 65 is covered by an absorbent material 67, such as a fibrous web, which forms the measuring field. The absorbent material 67 and the measuring field 32 lie in a recess 69 of the spacing layer 63, which recess has a longitudinal elongated oval shape (see also FIG. 2) and is larger than the measuring field 32. In the cover layer 61 is formed a drop application opening 71 defining the drop application field 33, which drop application opening 71 is displaced from the measuring field 32 and the absorbent material 67, so that it lies above a free space of the recess 69, as shown in FIG. 5. Therefore, the measuring field 32 is protected against the receipt of stray light by the cover layer 61.

An operating person uses the measuring device in the following way:

First, the device is prepared for a measurement in a way known in itself. Next, the cover 48 is opened. The head section 26 is separated from the test package 10 and the main section 24 is so placed onto the support surface 40 that the arresting pins 42 move into the notches 30. The portion of the test strip card extending out of the main section 24 lies ready to be gripped over the gripping depression 43. The cover 48 is then closed. Thus, the device is loaded and the test strip card is protected from moisture.

When a measurement is to be carried out, the cover 48 is opened and the test strip 20 is pulled so far out of the sleeve 12 that the nose 46 moves into the slot 34 directly following the pulled out test strip 20. The position of the nose 46 is so chosen that, in this position of the test strip card 18, the test field 32, which was previously protected in the sleeve 12, now lies over the measuring opening. In this position, an empty measurement of the test field 32 is carried out.

After this, the body fluid to be analyzed is dropped onto the drop application opening 71 as indicated in the FIG. 5 by the line 73. By capillary effect, the fluid is drawn into the absorbent material 67 of the test field 32. The eventual remaining fluid is taken up by the spacing layer 63, which likewise consists of an absorbent material, but whose absorption response is retarded from that of the absorbent material 67. The measured value delivered by the evaluation circuit appears in the indicator unit 42. At this point, the cover 48 is closed so that the separating elements of 46 become inserted into the slot 34 behind the entirely pulled out test strip 20. The used test strip 20 can then be removed by tearing it from the remainder of the cord. The previously described measuring process can then be repeated, so long as test strips are contained in the sleeve 12. Then a new step strip package 10 must be placed in the measuring device.

I claim:

1. A test strip for a measuring device for optically determining the concentration of a substance in a body fluid, especially for blood sugar measurement, with a carrier on which a measuring field including a first absorbent material is formed, characterized:

in that the carrier includes a bottom layer and a cover layer, which bottom layer and cover layer are separated from one another by a spacing layer;

in that in the bottom layer a pass through opening covered by the measuring field is provided for a measuring beam of a measuring optic system;

in that in the cover layer a drop application opening is formed, which drop application opening is so displaced from the measuring field that the measuring field and the drop application opening do not overlap;

in that the spacing layer has a recess including both the measuring field and the drop application opening, the absorbent material being located in the recess and covering the measuring field, but not extending to nor covering the drop application opening, so that a fluid applied through the drop application opening can flow freely through the recess from the drop application opening to the absorbent material; and in that the spacing layer is made of a second absorbent material having an absorption response retarded in comparison to that of the first absorbent material of the measuring field.

* * * * *